United States Patent
Noh et al.

(10) Patent No.: US 11,241,635 B2
(45) Date of Patent: Feb. 8, 2022

(54) METHOD AND SYSTEM FOR PROVIDING INTERACTIVE SERVICE USING SMART TOY

(71) Applicant: AURORA WORLD CORPORATION, Seoul (KR)

(72) Inventors: Heui Yul Noh, Seoul (KR); Myeong Ho Roh, Seongnam-si (KR); Chang Woo Ban, Yongin-si (KR); Oh Soung Kwon, Seongnam-si (KR); Seung Pil Lee, Namyangju-si (KR); Seung Min Shin, Gwangju-si (KR)

(73) Assignee: AURORA WORLD CORPORATION

( * ) Notice: Subject to any disclaimer, the term of this patent is extended or adjusted under 35 U.S.C. 154(b) by 0 days.

(21) Appl. No.: 16/961,951

(22) PCT Filed: Nov. 15, 2019

(86) PCT No.: PCT/KR2019/015627
§ 371 (c)(1),
(2) Date: Jul. 14, 2020

(87) PCT Pub. No.: WO2021/095935
PCT Pub. Date: May 20, 2021

(65) Prior Publication Data
US 2021/0308593 A1     Oct. 7, 2021

(30) Foreign Application Priority Data

Nov. 14, 2019 (KR) .................. 10-2019-0146031

(51) Int. Cl.
*A63H 3/28*    (2006.01)
*A63H 3/36*    (2006.01)
(Continued)

(52) U.S. Cl.
CPC ............. *A63H 3/28* (2013.01); *A61B 5/165* (2013.01); *A63H 3/365* (2013.01);
(Continued)

(58) Field of Classification Search
CPC .......... A63H 3/28; A63H 3/365; A61B 5/165; G06K 9/00268; G06T 3/4076; G06T 5/50; G10L 25/63
See application file for complete search history.

(56) References Cited

U.S. PATENT DOCUMENTS 11,043,230 B1 *    6/2021   Riding ................. G10L 25/63
2003/0108223 A1    6/2003   Prokoski
(Continued)

FOREIGN PATENT DOCUMENTS

| JP | 2003512684 A | 4/2003 |
| JP | 2010503110 A | 1/2010 |

(Continued)

OTHER PUBLICATIONS

Non-final Office Action (Notice of Preliminary Rejection) of the Korean Intellectual Property Office issued in Korean Patent Application No. 10-2019-0146031, dated Mar. 24, 2020 with English translation.

(Continued)

*Primary Examiner* — Qun Shen
(74) *Attorney, Agent, or Firm* — Harness, Dickey & Pierce, P.L.C.

(57) ABSTRACT

The present disclosure according to at least one embodiment relates to, in the learning process of a child using smart toys, a method and system for providing an interactive service by using a smart toy, which provide more accurate classified emotional state of the child based on at least one or more sensed data items of an optical image, a thermal image, and voice data of the child, as well as adaptively provide a (Continued)

flexible and versatile interactive service according to classified emotions.

11 Claims, 8 Drawing Sheets

(51) Int. Cl.
*A61B 5/16* (2006.01)
*G06K 9/00* (2006.01)
*G10L 25/63* (2013.01)
*G06T 3/40* (2006.01)
*G06T 5/50* (2006.01)
*G06N 20/00* (2019.01)
*H04N 5/33* (2006.01)

(52) U.S. Cl.
CPC ..... *G06K 9/00268* (2013.01); *G06K 9/00335* (2013.01); *G06N 20/00* (2019.01); *G06T 3/4076* (2013.01); *G06T 5/50* (2013.01); *G10L 25/63* (2013.01); *H04N 5/33* (2013.01); *A63H 2200/00* (2013.01)

(56) References Cited

U.S. PATENT DOCUMENTS

| | | | |
|---|---|---|---|
| 2008/0059156 A1* | 3/2008 | Han | G10L 15/08 704/207 |
| 2010/0174586 A1 | 7/2010 | Berg, Jr. et al. | |
| 2012/0232886 A1* | 9/2012 | Capuozzo | H04L 12/2814 704/9 |
| 2014/0347265 A1* | 11/2014 | Aimone | H04W 4/029 345/156 |
| 2017/0148433 A1* | 5/2017 | Catanzaro | G10L 15/183 |
| 2018/0144649 A1* | 5/2018 | el Kaliouby | G06F 16/337 |
| 2018/0314689 A1* | 11/2018 | Wang | G10L 15/07 |
| 2019/0042894 A1* | 2/2019 | Anderson | G06K 9/6257 |
| 2020/0410976 A1* | 12/2020 | Zhou | G06N 3/08 |

FOREIGN PATENT DOCUMENTS

| | | |
|---|---|---|
| KR | 1020170085732 A | 7/2017 |
| KR | 1020180130903 A | 12/2018 |
| KR | 20190098781 A | 8/2019 |

OTHER PUBLICATIONS

Non-final Office Action (Notice of Decision of Rejection) of the Korean Intellectual Property Office issued in Korean Patent Application No. 10-2019-0146031, dated Aug. 28, 2020 with English translation.

Decision to Grant of the Korean Intellectual Property Office issued in Korean Patent Application No. 10-2019-0146031, dated Oct. 19, 2020 with English translation.

First Office Action (in Korean) issued in Korean Application No. 10-2019-0146031, dated Mar. 24, 2020.

* cited by examiner

METHOD AND SYSTEM FOR PROVIDING INTERACTIVE SERVICE USING SMART TOY

CROSS-REFERENCE TO RELATED APPLICATIONS

This application is a U.S. National Phase Application under 35 U.S.C. 371 of International Application No. PCT/KR2019/015627, filed on Nov. 15, 2019, which claims priority under 35 U.S.C § 119(a) of Patent Application No. 10-2019-0146031, filed on Nov. 14, 2019 in Korea. The entire disclosures of the above applications are incorporated herein by reference. In addition, this non-provisional application claims priority in countries, other than the U.S., with the same reason based on the Korean patent application, the entire content of which is hereby incorporated by reference.

TECHNICAL FIELD

The present disclosure in some embodiments relates to a method and system for providing an interactive service by using a smart toy. More particularly, the present disclosure relates to a method and system for providing an appropriate interactive service more flexibly and efficiently according to children's emotional state identified through the use of smart toys.

BACKGROUND

The statements in this section merely provide background information related to the present disclosure and do not necessarily constitute prior art.

As rapidly expanding as the recent topic of the 4th Industrial Revolution is the rapid growth of content services to their extent based on information communication technology (ICT) and Internet of Things (IOT). Changing alongside generation change is the educational content paradigm. With the increasing importance of creativity-oriented educational content, interactive content is becoming increasingly more important.

In order to provide differentiated content services based on creativity learning, the necessity of two-way interactive educational technology is emerging. Existing infants' and toddlers' learning materials making use of the existing smart devices mostly let user equipment or a terminal one-sidedly lead the user who is only allowed to follow what is instructed. Such a lone user's play is destined to be bounded by the set pattern of play repeated over and over until it turns to be dullishly easy.

On the other hand, an educational game to diversify the instances of play if interactively played would give the user better opportunities to think. To this end, an educational content platform is needed for creative learning in the form of a new learning system in which smart terminals participate in the user-led play patterns. For example, there is a need for a technology of analyzing shapes according to the configuration, movement and other states of dolls and props, while recognizing users' emotions according to their voices and expressions, and for a technology of structuring a flexible learning server for the analyzing and recognizing technology.

SUMMARY

Technical Problem

The present disclosure in some embodiments aims to contribute to the learning process of a child using smart toys by providing improved accuracy of classifying the child's current emotional state based on at least one sensed data item of an optical image, a thermal image, and voice data of the child while providing flexible and diverse interactive services according to the classified emotions.

Technical Solutions

At least one embodiment of the present disclosure provides a smart toy system including a smart toy, a service platform apparatus, and a user terminal. The smart toy is configured to use at least one sensor to collect at least one or more sensed data items of an optical image, a thermal image, and voice data of a child currently in play. The service platform apparatus is configured to receive the sensed data items, to generate classified emotion information after classifying a current emotional state of the child, and to extract and provide an interactive service corresponding to the classified emotion information. The user terminal is configured to receive personalized content provided according to the interactive service.

Another embodiment of the present disclosure provides a method performed by a smart toy system for providing an interactive service, the method including collecting, by a smart toy utilizing at least one sensor, at least one or more sensed data items of an optical image, a thermal image, and voice data of a child currently in play, and receiving, by a service platform apparatus, the sensed data items to generate classified emotion information after classifying a current emotional state of the child and to extract and provide the interactive service corresponding to the classified emotion information, and receiving, by the smart toy and a user terminal, the interactive service that is provided.

Advantageous Effects

As described above, in the learning process of a child using smart toys, the present disclosure in some embodiments provides improved accuracy of classifying the child's current emotional state based on at least one sensed data item of an optical image, a thermal image, and voice data of the child while providing flexible and diverse interactive services according to the classified emotions.

| REFERENCE NUMERALS | |
| --- | --- |
| 100: smart toy system | 110: smart toy |
| 120: service platform apparatus | 130: user terminal |

-continued

| REFERENCE NUMERALS | |
|---|---|
| 300: learning model unit | 310: service provider |
| 320: content provider | |

DETAILED DESCRIPTION

Hereinafter, some embodiments of the present disclosure will be described in detail with reference to the accompanying drawings. In the following description, a detailed description of known functions and configurations incorporated therein will be omitted for the purpose of clarity and for brevity.

Throughout this specification, when a part "includes" or "comprises" a component, the part is meant to further include other components, not to exclude thereof unless specifically stated to the contrary. The terms such as "unit," "module," and the like refer to one or more units for processing at least one function or operation, which may be implemented by hardware, software, or a combination thereof.

The present disclosure provides a learning system as an educational content platform for creative learning, in which a smart terminal participates in a user-led play pattern.

In addition, the present disclosure provides a platform system with various multi-subsystems made available, including a mobile application system for utilizing smart toys, a server system, and an analysis system utilizing big data.

According to the present disclosure, a user may be provided with flexible and various interactive services responsive to emotions induced through smart toy centered play.

Figure 1:
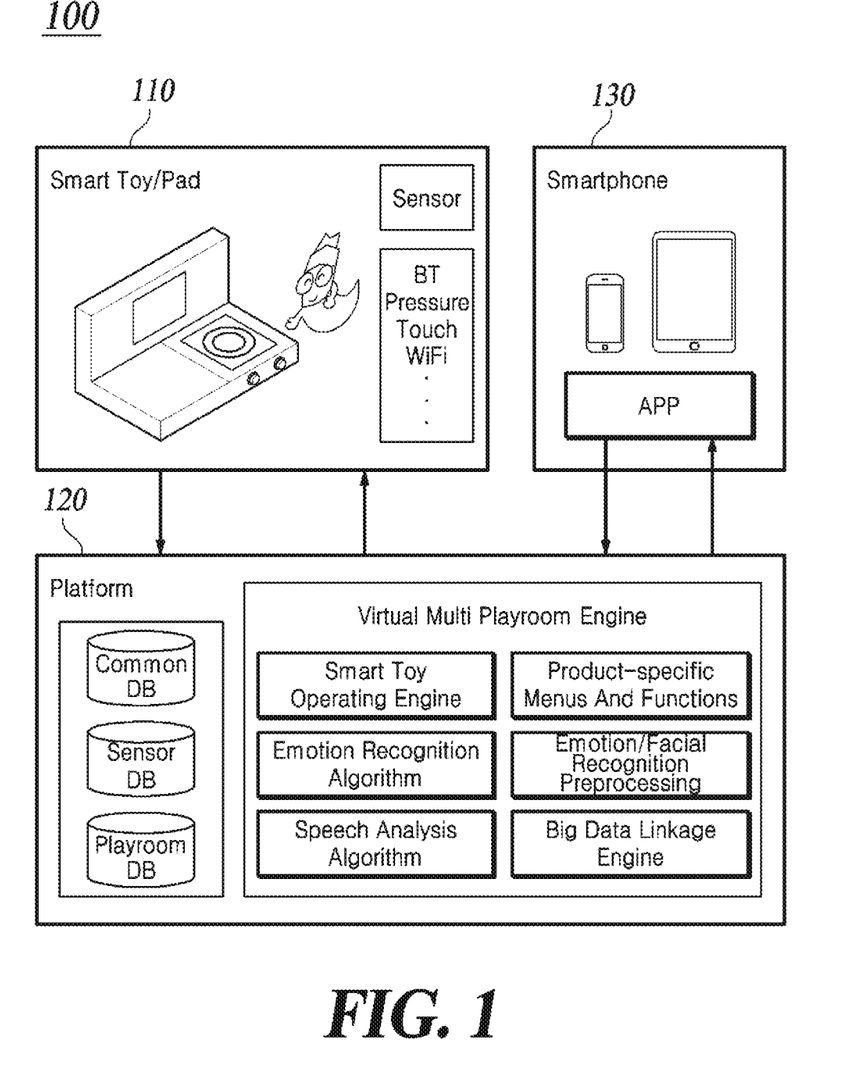
FIG. 1 is a diagram of a smart toy system according to at least one embodiment of the present disclosure.

FIG. 1 is a diagram of a smart toy system according to at least one embodiment of the present disclosure.

As shown in FIG. 1, the smart toy system 100 according to at least one embodiment of the present disclosure includes a smart toy 110, a service platform apparatus 120, and a user terminal 130. Here, the components included in the smart toy system 100 are merely illustrative of the technical idea of at least one embodiment, and those of ordinary skill in the art to which the embodiments of the present disclosure belongs may implement the present disclosure with various modifications and variations applied to the components included in the smart toy system 100 without departing from the principal ideas of the embodiments.

The smart toy 110 refers to a device that is an infant child's or child's play object and capable of supporting adaptive two-way communications responsive to the emotion recognition of the child. The smart toy 110 may be implemented by various types of play equipment such as a toy doll.

In at least one embodiment, the smart toy 110 is a kind of 'phygital' toy that is a combined physical and digital technology toy. In other embodiments, it is a connected toy that works in conjunction with smartphone and tablet computer software applications or apps.

The smart toy 110 is provided with at least one sensor and collects sensed data about a child currently playing by using the provided sensor. Meanwhile, in at least one embodiment, the smart toy 110 may collect at least one of an optical image, a thermal image, and voice data as sensed data of the child. In addition, at least one embodiment further collects the behavior pattern of the child. At this time, the behavior pattern of the child may be at least the position information, motion information and state information of the smart toy 110 in relation to the current play of the child.

To this end, the smart toy 110 may be provided with a hardware module such as a vision camera for optical images, an infrared camera for thermal images, a microphone, a motion sensor, or the like.

The smart toy 110 transmits the collected sensed data to the service platform apparatus 120 and receives therefrom an interactive service offered according to the child's classified emotional state based on the sensed data. In this case, the interactive service provided to the smart toy 110 maybe, a kind of interaction scenario that is, for example, interaction behavior information including at least one or more of an utterance gesture and an expression of the smart toy. For example, the smart toy 110 may express specific audio/text, facial expressions, gesture data, etc. according to an interactive service supplied by the service platform apparatus 120.

The service platform apparatus 120 interoperates with the smart toy 110 and the user terminal 130 and performs a function of extracting and providing an interactive service for a child based on sensed data collected from the smart toy 110.

Figure 2:
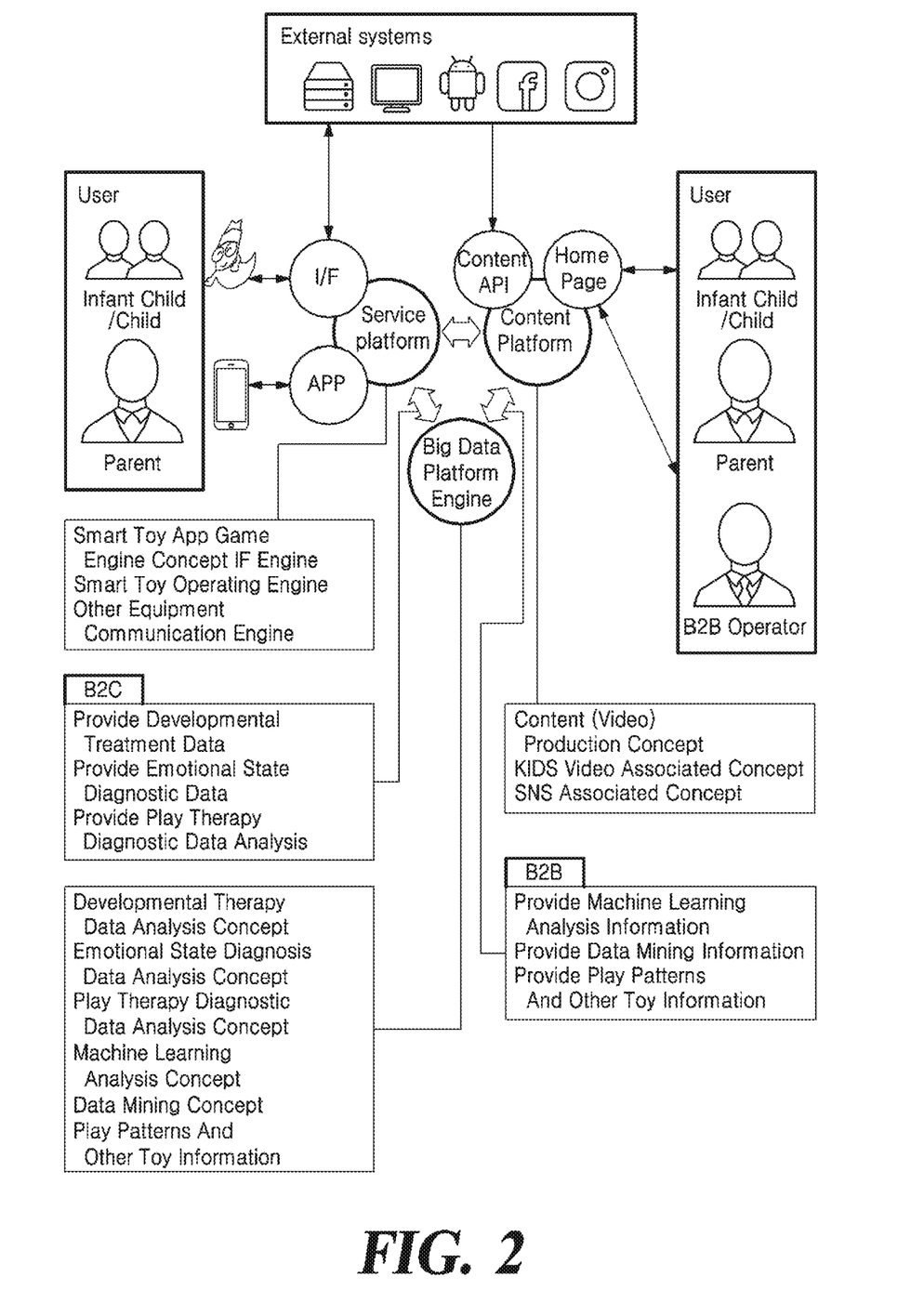
FIG. 2 is a diagram of an example interactive service according to at least one embodiment of the present disclosure.
Figure 3:
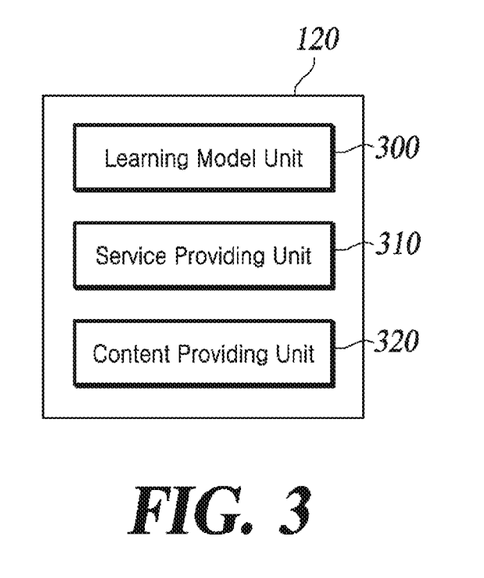
FIG. 3 is a schematic block diagram of a service platform apparatus according to at least one embodiment of the present disclosure.

FIG. 2 is a diagram of an example interactive service according to at least one embodiment. FIG. 3 is a schematic block diagram of a service platform apparatus according to at least one embodiment.

Hereinafter, referring to FIG. 2 and FIG. 3 together, the function of the service platform apparatus 120 according to at least one embodiment will be described.

As shown in FIG. 2, the service platform apparatus 120 according to at least one embodiment provides a novel educational content environment based on various convergence technologies encompassing traditional toys, contents, ICT technologies, and others.

According to at least one embodiment, the service platform apparatus 120 provides a big data-based smart platform environment that may check the emotional state of the child based on the sensed data of the child collected through the smart toy 110 and provide an interactive service corresponding to the emotional state confirmed. Such a service platform apparatus 120 allows a platform service covering a guardian and a B2B operator as well as the target child learner to be provided.

For example, the service platform apparatus 120 is adapted to generate an interactive action command for controlling the operation of the smart toy 110 according to the child's emotional state classified based on the sensed data of the child collected from the smart toy 110 and to perform a two-way communication service function provided by the smart toy 110.

In addition, the service platform apparatus 120 may provide the guardian with the child's emotional state it generated or perform a personalized content capability that generates and provides personalized content suitable for the current emotional state of the child through interworking with an external device.

To this end, the service platform apparatus 120 according to at least one embodiment provides a learning model unit 300, a service providing unit 310, and a content providing unit 320 as shown in FIG. 3.

The learning model unit 300 provides at least one learning model that underwent previous learning. The learning model unit 300 provides functions of checking the emotional state of the child, storing at least one learning model that underwent previous learning of various data required until the learning model unit 300 can yield an interactive service suitable for the emotional state confirmed, and providing the stored learning model when necessary.

For example, the learning model unit 300 according to at least one embodiment includes at least an analysis model, an emotion classification model, and an output model. The analysis model is provided for recognizing and analyzing data related to the emotional state classification in the sensed data collected from the smart toy 110. The emotion classification model is provided for classifying a child's emotional state according to the analysis result of the analysis model. The output model is provided for yielding an appropriate interactive service according to the classification result of the emotion classification model.

In addition, at least one embodiment does not limit the learning model provided on the learning model part 300 to a specific learning model.

The service provider 310 performs the functions of generating classified emotion information after classifying the current emotional states of the child based on the sensed data collected from the smart toy 110 and extracting and providing a suitable interactive service for the generated classified emotion information.

The service provider 310 according to at least one embodiment is responsible for providing a service related to two-way communications between the child and the smart toy 110 among the interactive services provided through the service platform apparatus 120. Here, the interactive service yielded by the service provider 310 may be a kind of interaction scenario between the child and the smart toy 110, which is, for example, interaction behavior information offered including at least one or more of an utterance gesture and an expression of the smart toy.

The following describes a process performed by the service providing unit 310 for generating classified emotion information after classifying the current emotional state of the child based on the sensed data collected from the smart toy 110.

The service provider 310 according to at least one embodiment of the present disclosure is adapted to collect at least one sensed data of an optical image, a thermal image, and voice data of the child from the smart toy 110, and to classify, based on the sensed data, the current emotional state of the child.

For example, the service provider 310 may classify the current emotional state of the child based on the optical image and the thermal image. More particularly, the service provider 310 may generate classified emotion information through a deep or refined classification of the current emotional state of the child (into fine classified information as described hereinafter) on the basis of the optical image and the thermal image and based on the predefined basic emotion information.

To this end, the service provider 310 may primarily extract feature points related to the child's face out of the optical image and use the extracted feature points as a basis for carrying out a primary classification of the current emotional state information of the child to generate basic emotion information.

Figure 4:
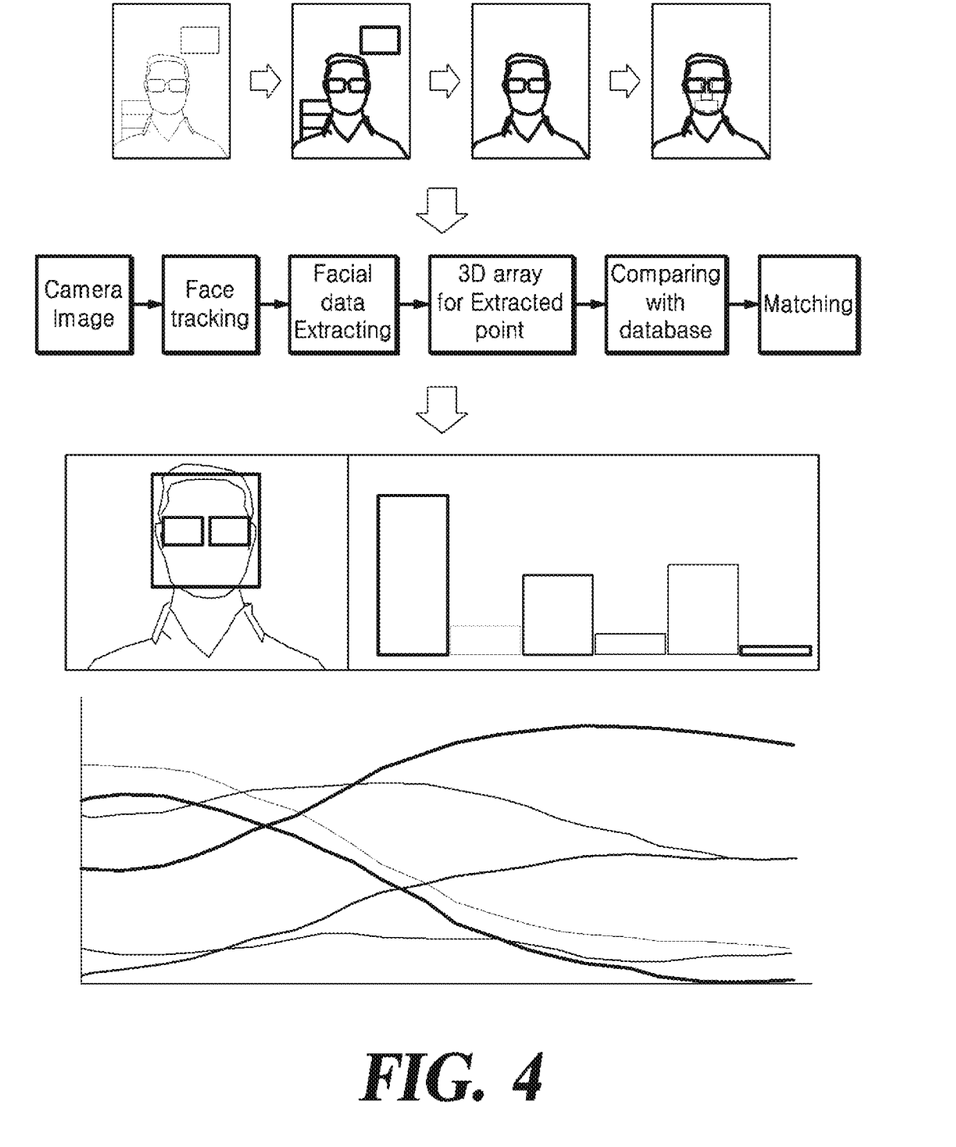
FIG. 4 to FIG. 8 are diagrams for explaining a method of generating classified emotion information according to some embodiments of the present disclosure.

For example, as shown in FIG. 4, the service provider 310 tracks the position of the face in the optical image by using at least normalization, binarization, outline extraction, and a recognition classifier.

The service provider 310 first converts the optical image to grayscale and then extracts, from the image, a boundary line and thereby extracts feature points such as eyes, nose, mouth, forehead, and cheekbone.

The service provider 310 converts the extracted feature point values into a two-dimensional matrix and then converts the two-dimensional matrix into a three-dimensional matrix by using a camera focus value.

The service provider 310 extracts value for a facial expression by using an algorithm using learning data learned by a learning machine from the converted matrix value and classifies the accuracy of each emotion to generate basic emotion information. At this time, the basic emotion information is the most basic information related to the emotional state of the child, for example, maybe a result of primary emotions classified such as joy, sadness, anger, and the like.

The service provider 310 performs an emotion refinement and analysis process on a thermal image by measuring heat/temperature at a predefined specific region of the thermal image and quantifying the basic emotion information previously generated based on the measured heat/temperature information to generate refined emotion information. The predefined specific region may be determined differently according to the basic emotion information.

According to the degree of emotional state, the heat/temperature of a person may have different values. For example, with a surge of anger, heat/temperature of a specific body part accordingly changes. In view of this, the service provider 310 may extract heat/temperature of a specific part based on the basic emotion information and generate refined emotion information by reflecting the heat/temperature.

Figure 5:
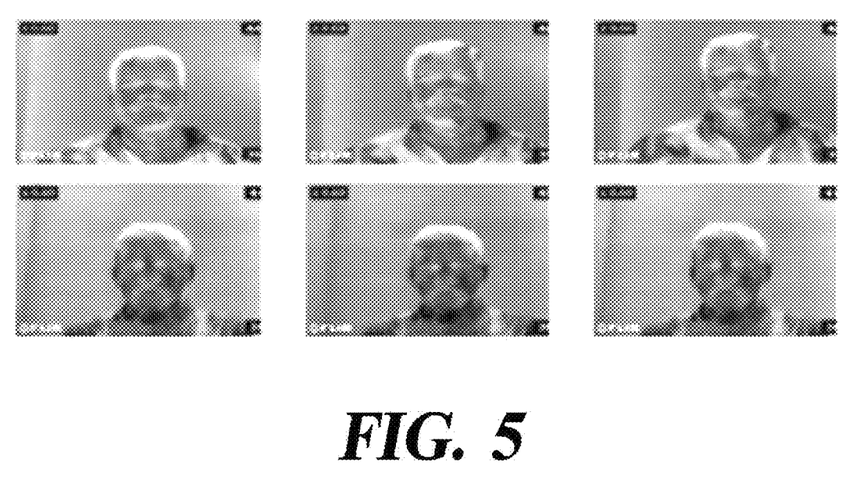

For example, as shown in FIG. 5, the service provider 310 recognizes the position of a face in a thermal image by referring to the position of the face detected in an optical image.

The service provider 310 sets regions of interest in the position of the recognized face to extract temperature values of feature points such as eyes, nose, mouth, cheekbone, and forehead and presents the quantified degree of basic emotion information based on the extracted temperature values and thereby generates refined emotion information. In this case, the service provider 310 may utilize a predefined emotion classification graph.

Meanwhile, the service providing unit 310 may generate a 3D composite image by synthesizing the optical image and the thermal image in the process of classifying the current emotional state of the child based on the optical image and the thermal image and may generate refined emotion information based on the generated 3D composite image.

On the other hand, the difficulty to introduce a high-resolution thermal camera in extracting the heat/temperature of a specific region through the conventional thermal image may result in a low-resolution error in the temperature measurement in relation to distance due to emissivity in the air.

With this in mind, the service provider 310 according to at least one embodiment generates a 3D composite image by synthesizing the optical facial image and thermal image and generates the refined emotion information based on heat/temperature information that underwent a temperature correction in relation to distance based on the generated 3D composite image, resulting in an improved accuracy of the emotion classification.

Figure 6:
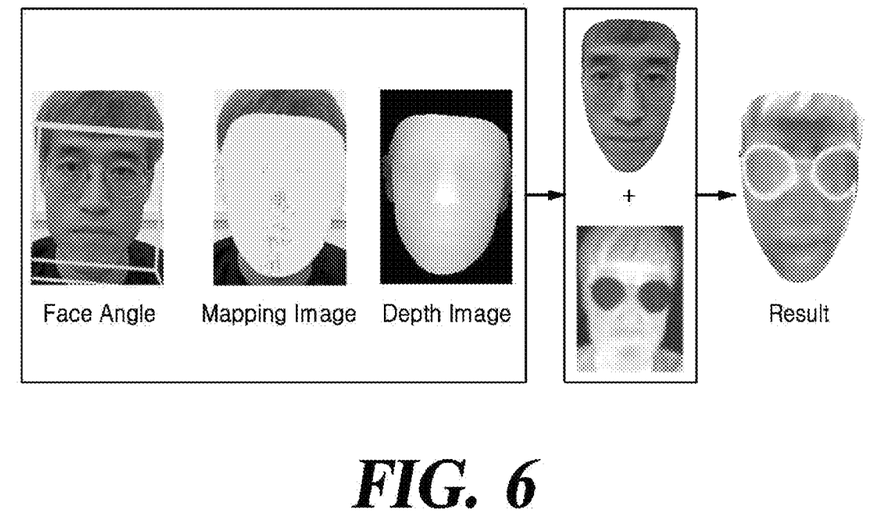
Figure 7:
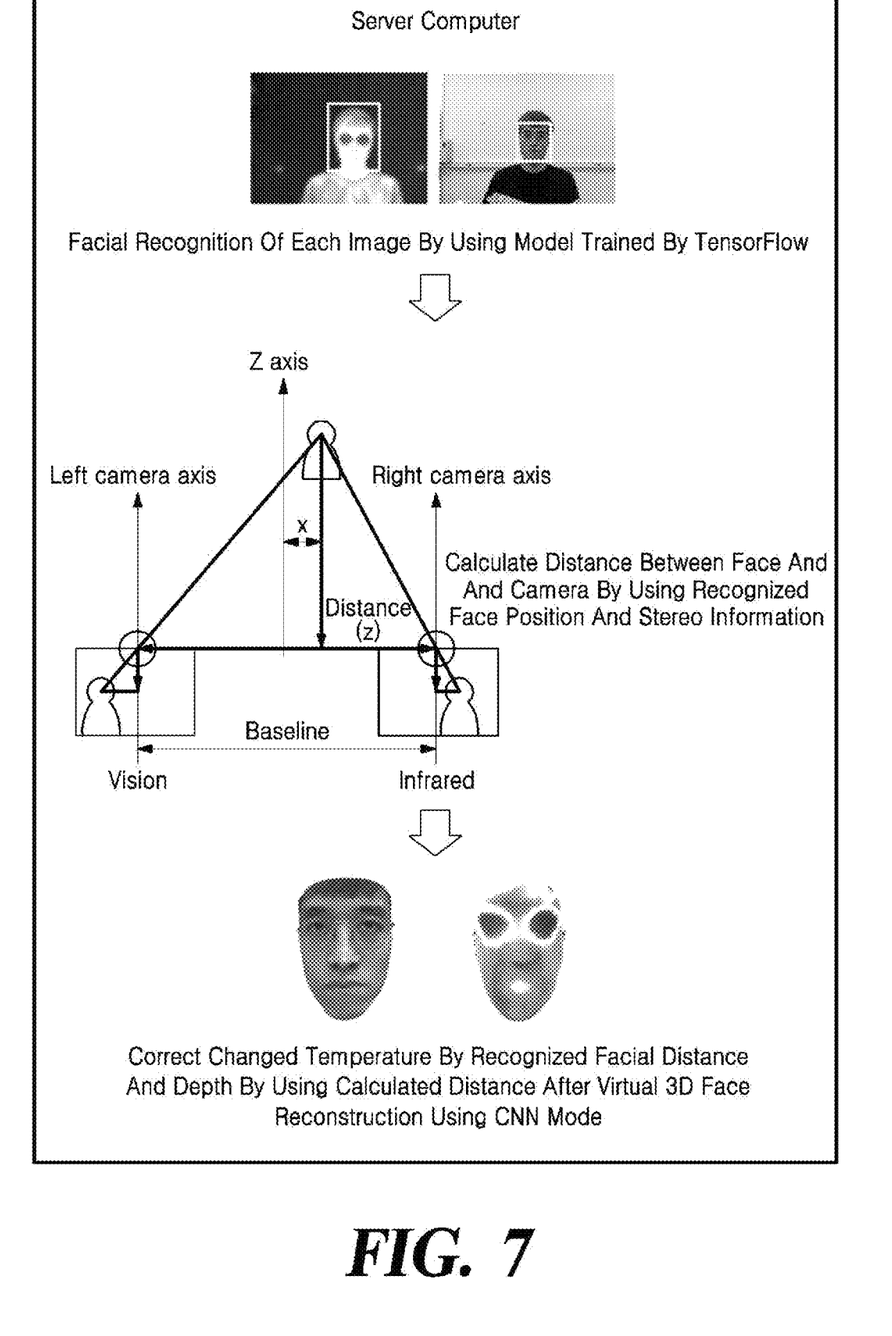

For example, as shown in FIGS. 6 and 7, the service provider 310 may three-dimensionally reconstruct the optical facial image from virtual 3D face data trained through the learning model and merge the reconstructed optical facial image with a thermal image registered with the optical image in scale to generate a 3D composite image.

In this process, the service provider 310 may further perform a process of restoring the low-pixel thermal image to the high-pixel equivalent with reference to the optical image.

Subsequently, the service providing unit 310 performs a correction to temperature alteration by the distance and depth of the recognized face by using the calculated distances between the vision and infrared cameras and the recognized face, thereby resolving the conventional error issue in the temperature measurement in relation to distance.

Meanwhile, the service provider 310 according to at least one embodiment further uses voice data collected from the smart toy 110 in the process of classifying the current emotional state of the child.

In particular, the service provider 310 may further classify the current emotional state of the child based on the voice data to generate subtle classified information and provide the generated subtle classified information as the classified emotion information.

The service provider 310 may generate subtle classified information by combining the child's emotional state classified based on the voice data with the child's emotional state classified earlier based on the optical image and the thermal image.

Figure 8:
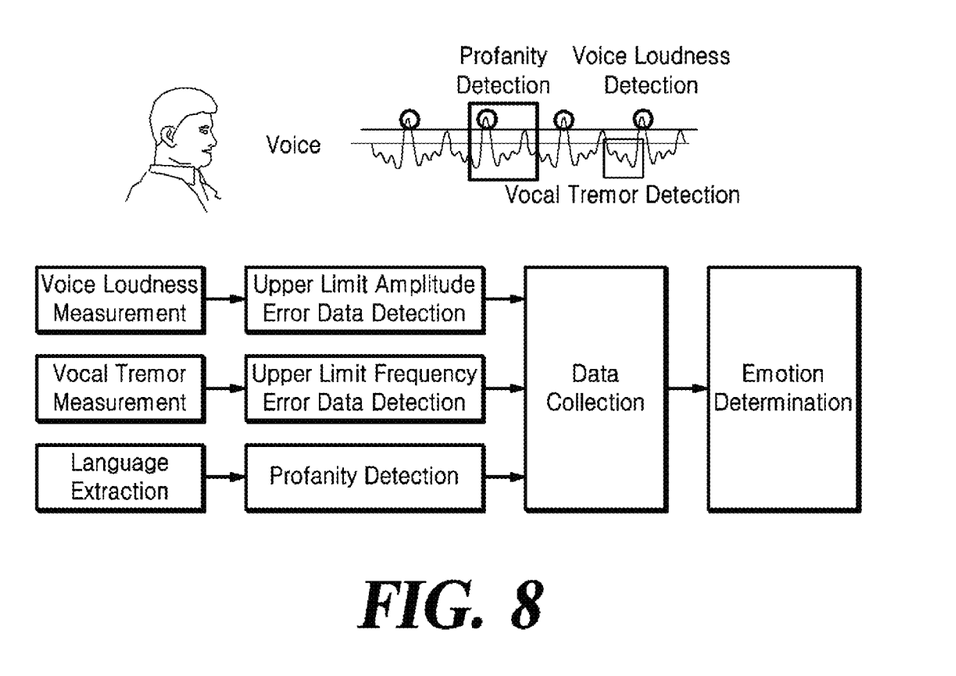

To this end, the service providing unit 310 may determine the emotional state of the child by analyzing the voice data, as shown in FIG. 8. For example, the service provider 310 may analyze the voice data to extract and collect the voice loudness, the vocal tremor, the language, and the like, and may determine the child's emotional state based on the collected data.

The service provider 310 may perform a preprocessing process on the voice data in the analyzing of the voice data and the determining of the child's emotional state. For example, the service provider 310 may perform a normalization of the collected voice data in tune with a predefined voice frequency of the child. The service provider 310 may generate a general voice frequency band of the child based on a model trained in advance based on the voice data of the child and proceed with the frequency normalization process by using the provided general voice frequency band.

In the process of classifying the current emotional state of the child, the service provider 310 according to at least one embodiment further receives the behavior pattern of the child as sensed data and additionally utilizes the same to generate the classified emotion information.

The service provider 310 yields an interactive service related to two-way communications between the child and the smart toy 110 based on the classified emotion information generated and the learning model in the learning model unit 300, and it provides the calculated interactive service to the smart toy 110. The service provider 310 may yield, as the interactive service, the interaction behavior information offered including at least one or more of the utterance gesture and the expression of the smart toy 110 based on the classified emotion information.

The content provider 320 is responsible for providing a personalized content service among the interactive services provided through the service platform apparatus 120.

According to at least one embodiment of the present disclosure, the content providing unit 320 generates the personalized content based on the classified emotion information after classification through the service providing unit 310 and provides the personalized content to the user terminal 130 as an interactive service.

The content provider 320 may receive classified emotion information from the service provider 310 and transmit the classified emotion information to an external device and may receive, from the external device, personalized content corresponding to the classified emotion information as an interactive service.

The user terminal 130 refers to a device that receives a personalized content service among interactive services provided by the service platform apparatus 120. The user terminal 130 may be a smartphone or the like owned by the parents of the child.

In addition to the personalized content, the user terminal 130 may be provided with state alarm information related to the emotional state of the child.

Figure 9:
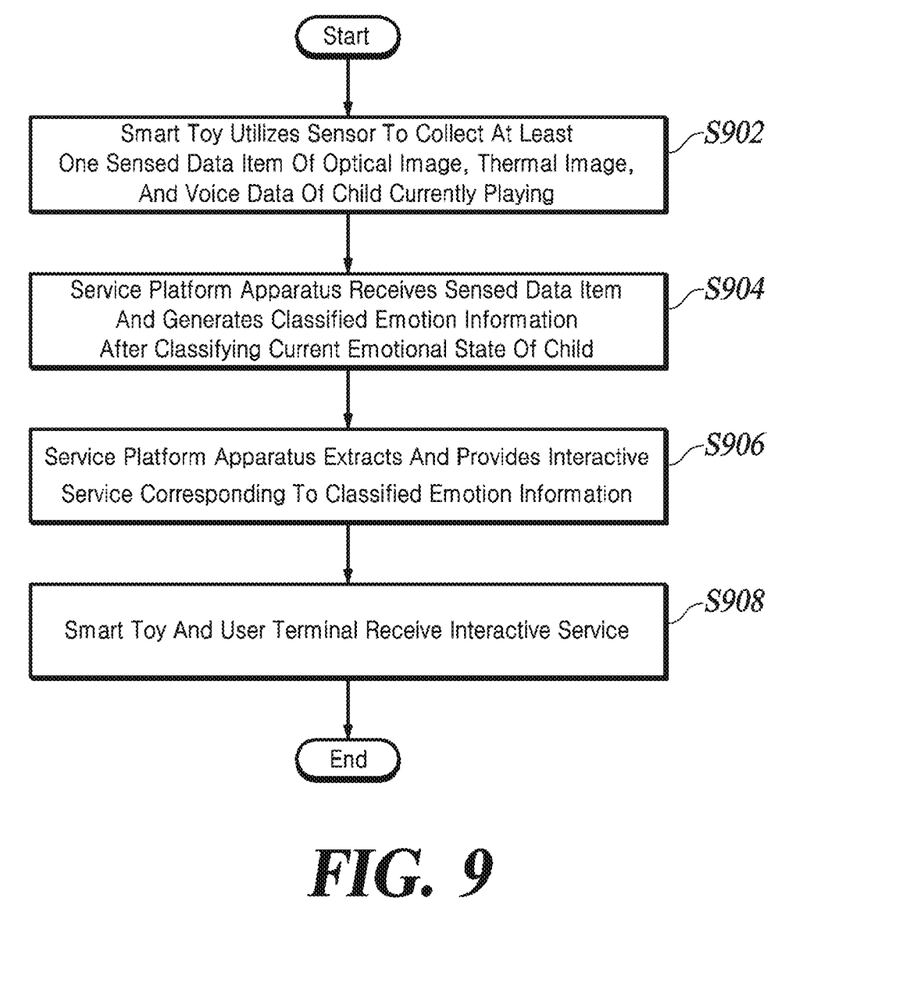
FIG. 9 is a flowchart of a method of providing an interactive service of a smart toy system according to at least one embodiment of the present disclosure.

FIG. 9 is a flowchart of a method of providing an interactive service of a smart toy system according to at least one embodiment of the present disclosure.

The smart toy 110 utilizes one or more provided sensors to collect at least one or more sensed data items of an optical image, a thermal image, and voice data of the child currently in play (in Step S902). In Step S902, the smart toy 110 may additionally collect behavior patterns of the child as the sensed data.

The service platform apparatus 120 receives the sensed data items collected in Step S902 and generates classified emotion information after classifying the child's current emotional state (S904). In Step S904, the service platform apparatus 120 may generate the classified emotion information through a deep or fine classification of the child's emotional state on the basis of the optical image and the thermal image and based on the predefined basic emotion information.

The service platform apparatus 120 may further classify the child's emotional state based on the voice data to generate subtle classified information and may provide the generated subtle classified information as the classified emotion information.

The service platform apparatus 120 may further receive the behavior pattern for the child as sensed data and may generate classified emotion information by further using the same data.

The service platform apparatus 120 in Step S906 extracts and provides an interactive service corresponding to the classified emotion information generated in Step S904. In Step S906, the service platform apparatus 120 may output, as the interactive service, the interaction behavior information including at least one or more of the utterance gesture and the expression of the smart toy 110 based on the classified emotion information.

In addition, the service platform apparatus 120 may interwork with the external device to extract personalized content corresponding to the classified emotion information as the interactive service.

The smart toy 110 and the user terminal 130 receive the provided interactive service from the service platform apparatus 120 (S908).

Here, Steps S902 to S908 correspond to the operations of the respective components of the smart toy system described above, and thus a further detailed description thereof will be omitted.

Although the steps in FIG. 9 are described to be sequentially performed, they not necessarily limited thereto. Various modifications, additions, and substitutions are possible by changing the sequence in FIG. 9 or by performing two or more of the steps in parallel, and hence the steps in FIG. 9 are not limited to the illustrated chronological sequence.

As described above, the method of providing interactive services of the smart toy system described in FIG. 9 may be implemented in a computer program and recorded on a computer-readable recording medium. The computer-readable recording medium recorded with a computer program for implementing the method of providing interactive services of the smart toy system may include any types of storage devices on which data that can be read by computer software are recordable. Such computer-readable recording medium may be a non-transitory medium such as a ROM, RAM, CD-ROM, magnetic tape, floppy disk, optical data storage device, and the like, and may further include a transitory medium, such as a carrier wave (e.g., transmission over the Internet) and a data transmission medium. Further, the computer-readable recording medium can be distributed in computer systems connected via a network, wherein computer-readable codes can be stored and executed in a distributed mode.

Although exemplary embodiments of the present disclosure have been described for illustrative purposes, those skilled in the art will appreciate that various modifications, additions, and substitutions are possible, without departing from the idea and scope of the claimed invention. Therefore, exemplary embodiments of the present disclosure have been described for the sake of brevity and clarity. The scope of the technical idea of the present embodiments is not limited by the illustrations. Accordingly, one of ordinary skill would understand the scope of the claimed invention is not to be limited by the above explicitly described embodiments but by the claims and equivalents thereof.

The invention claimed is:

1. A smart toy system, comprising:
a smart toy configured to use at least one sensor to collect at least one or more sensed data items of an optical image, a thermal image, and voice data of a child currently in play;
a service platform apparatus configured to receive the sensed data items, to generate classified emotion information after classifying a current emotional state of the child, and to extract and provide an interactive service corresponding to the classified emotion information; and
a user terminal configured to receive personalized content provided according to the interactive service,
wherein the service platform apparatus comprises:
a learning model unit configured to provide at least one learning model trained in advance based on a plurality of data for checking the emotional state of the child and extracting the interactive service; and
a voice data preprocessing unit configured to extract and collect all or part of voice loudness, voice tremor and language from the voice data as a part of the classified emotion information,
wherein the learning model unit is configured to have a model, as one of the learning models trained in advance based on another voice data of a child to perform a normalization of the voice data in tune with a predefined voice frequency of a child,
wherein the service platform apparatus is configured to restore the thermal image of lower pixel resolution to an equivalent image of higher pixel resolution with reference to the optical image.

2. The smart toy system of claim 1, wherein the service platform apparatus comprises:
a service providing unit configured to generate the classified emotion information by using the learning model and to provide the interactive service related to two-way communications between the child and the smart toy; and
a content providing unit configured to generate the personalized content corresponding to the classified emotion information and providing the personalized content as the interactive service.

3. The smart toy system of claim 1, wherein the service platform apparatus is configured
to generate interactive behavior information including at least one or more of an utterance, a gesture, and an expression of the smart toy based on the classified emotion information, or to interwork with an external device to receive the personalized content corresponding to the classified emotion information and provide the personalized content as the interactive service.

4. The smart toy system of claim 1, wherein the service platform apparatus is configured to generate, based on the optical image and the thermal image, the classified emotion information by finely classifying the current emotional state of the child based on basic emotion information that is predefined.

5. The smart toy system of claim 4, wherein the service platform apparatus is configured to extract a feature point related to a face of the child out of the optical image and to provide the basic emotion information by primarily classifying current emotional state information of the child based on an extracted feature point.

6. The smart toy system of claim 4, wherein the service platform apparatus is configured
to perform an emotion refinement and analysis process on the thermal image by measuring heat/temperature at a predefined specific region and quantifying a degree of the basic emotion information based on information on the heat/temperature measured,
to generate refined emotion information, and
to provide the refined emotion information as the classified emotion information.

7. The smart toy system of claim 6, wherein the service platform apparatus is configured
to generate a 3D composite image by synthesizing the optical image and the thermal image, and
to generate the refined emotion information based on heat/temperature information that underwent a temperature correction in relation to distance between the smart toy and the child based on the 3D composite image.

8. The smart toy system of claim 4, wherein the service platform apparatus is configured to further classify the current emotional state of the child based on the voice data to generate subtle classified information and to provide the subtle classified information as the classified emotion information.

9. The smart toy system of claim 8, wherein the service platform apparatus is configured to generate the subtle classified information by combining a child's classified emotional state based on the voice data with a child's classified emotional state based on the optical image and the thermal image.

10. The smart toy system of claim 1, wherein
the smart toy is configured to further collect a behavior pattern of the child as the sensed data item, and
the service platform apparatus is configured to generate the classified emotion information by further considering a child's emotional state classified based on the behavior pattern.

11. A method performed by a smart toy system for providing an interactive service, the method comprising:

collecting, by a smart toy utilizing at least one sensor, at least one or more sensed data items of an optical image, a thermal image, and voice data of a child currently in play;
child currently in play;
receiving, by a service platform apparatus, the sensed data items to generate classified emotion information after classifying a current emotional state of the child, and to extract and provide the interactive service corresponding to the classified emotion information; and
receiving, by the smart toy and a user terminal, the interactive service that is provided,
   wherein the receiving the sensed data items to extract and provide the interactive service further comprising:
   providing at least one learning model trained in advance based on a plurality of data for checking the emotional state of the child,
preprocessing through extracting and collecting all or part of voice loudness, voice tremor and language from the voice data as a part of the classified emotion information, and
   restoring the thermal image of lower pixel resolution to an equivalent image of higher pixel resolution with reference to the optical image,
wherein one of the learning models is a model which trained in advance based on another voice data of a child to perform a normalization of the voice data in tune with a predefined voice frequency of a child.

\* \* \* \* \*